United States Patent [19]

Zahorsky

[11] 4,217,904
[45] * Aug. 19, 1980

[54] DRAIN CONSTRUCTION

[76] Inventor: Carroll L. Zahorsky, 4706 Broadway, Kansas City, Mo. 64112

[*] Notice: The portion of the term of this patent subsequent to Feb. 13, 1996, has been disclaimed.

[21] Appl. No.: 969,488

[22] Filed: Dec. 14, 1978

Related U.S. Application Data

[63] Continuation-in-part of Ser. No. 781,167, Mar. 25, 1977, Pat. No. 4,139,012.

[51] Int. Cl.² ............................................. A61M 27/00
[52] U.S. Cl. ................................................. 128/350 R
[58] Field of Search ............................ 128/348–351, 128/240, 245, 276–278; 32/33

[56] References Cited

U.S. PATENT DOCUMENTS

| 2,286,462 | 6/1942 | Chaffin | 128/350 R |
| 2,624,341 | 1/1953 | Wallace | 128/350 R |
| 3,421,510 | 1/1969 | Kettenbach | 128/350 R |
| 3,430,631 | 3/1969 | Abramson | 128/350 R |
| 3,516,410 | 6/1970 | Hakim | 128/350 R |
| 4,139,012 | 2/1979 | Zahorsky | 128/350 R |

Primary Examiner—Dalton L. Truluck
Attorney, Agent, or Firm—Lowe, Roker, Kircher, Wharton & Bowman

[57] ABSTRACT

A surgical drain is the subject of the present invention. A dual tubular construction is provided with openings along each tube on the side which is facing the other tube. Barrier means is provided and extends lengthwise of the two tubular members. The barrier means inhibits the entry of loose material which would clog the openings and restrict the flow of fluid. It further inhibits occlusion of the openings by attached impinging tissue or structures.

7 Claims, 6 Drawing Figures

DRAIN CONSTRUCTION

This application is a continuation-in-part of pending application Ser. No. 781,167, filed Mar. 25, 1977 now U.S. Pat. No. 4,139,012, issued Feb. 13, 1979.

This invention relates generally to drain constructions, and, more particularly, to a device for draining fluid from a congested area where there is a likelihood of material clogging the drain.

A perpetual problem with any type of drain device is that of the drain becoming clogged with loose material, or collapsing structure onto the drain openings, thereby restricting or completely blocking the flow of fluid into the drain. In many types of structural and geographical drain installation clogging often requires time-consuming and costly repair procedures. The problem also exists with regard to surgeons' drains which are commonly placed in a body cavity following surgery to remove excessive and undesirable fluids. In some instances accumulation of excessive fluid can have severe deleterious effects on the patient and may even be fatal.

In any type of surgery, even partial blockage of the surgical drain may result in excessive clotting of the blood and the formation of attendant scar tissue.

Others have directed efforts toward designing a surgical drain which will not obstruct. The prior designs have, however, invariably resulted in drains which were significantly less efficient because of the shielding used to protect the drain openings. In addition, in many cases the shields themselves have been susceptible to clogging thus preventing passage of fluid into the drain openings even though the latter may be clear.

It is therefore a primary object of the present invention to provide an improved drain for use in congested areas where loose material or impinging structure may clog the drain openings, which improved drain substantially precludes clogging without rducing the drainage efficiency.

As a corollary to the above object, a principal aim of the invention is to provide an improved drain for use in surgical applications wherein deleterious effects of accumulated fluids are avoided by assuring adequate and continual drainage of the fluids.

It is an important objective of this invention to provide an improved drain construction for use by surgeons which will permit more efficient irrigation of the cavity being drained.

Still another important object of the invention is to provide improved drain construction for use in congested areas where material may clog the drain openings, which improved drain may be designed to have a drainage capacity exceeding that of conventional drains even when the latter are properly functioning.

Other objects of the invention will be made clear or become apparent from the following description and claims when read in light of the accompanying drawing wherein:

Figure 1:
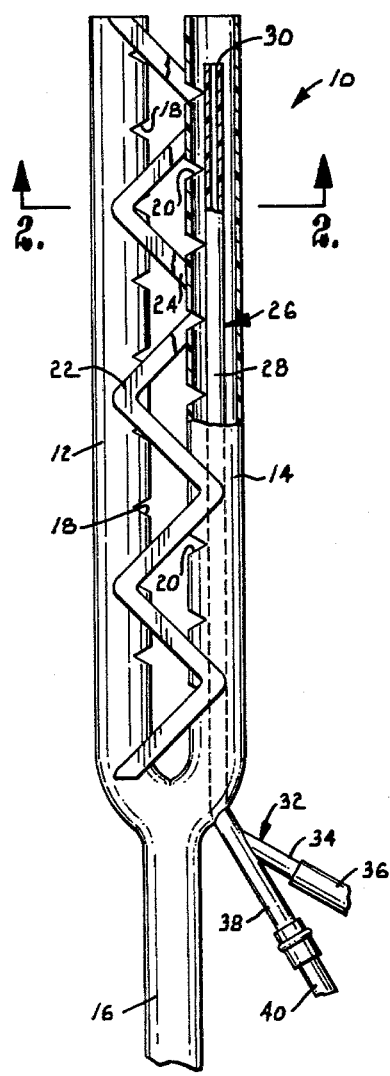
FIG. 1 is a side elevational view, partially in cross-section, of one form of the improved drain device of the present invention.

Referring initially to FIG. 1, the improved drain device of the present invention is designated generally by the numeral 10. Device 10 comprises a tubular member formed from first and second elongated cylindrical tubular sections 12 and 14 respectively. Sections 12 and 14 are open at one end and the opposite ends are coupled in fluid relationship to a common third tubular section 16. Third tubular section 16 is also preferably of elongated cylindrical configuration and may be of the same or slightly larger diameter than each of sections 12 and 14.

Figure 2:
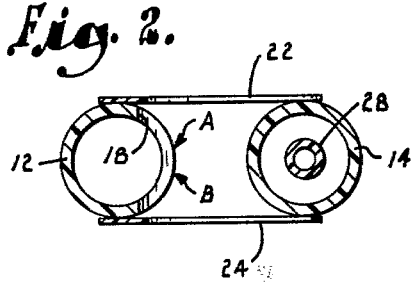
FIG. 2 is a horizontal cross-sectional view taken along a line 2—2 of FIG. 2.
Figure 4:
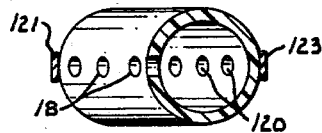
FIG. 4 is a horizontal cross-sectional view taken along line 4—4 of FIG. 3.

Each of sections 12 and 14 is provided with a plurality of openings disposed along its length which openings are located on one side of the section between parallel imaginary planes extending through opposed tangential points on the surface of the respective sections. This is best illustrated in FIG. 2. Manifestly, the openings 20 in section 14 are disposed in facing relationship to the openings 18 in the section 12. While the openings 18 and 20 may be of any desired configuration, a preferred configuration for maximum drainage efficiency is that illustrated in FIG. 1 wherein the openings have a generally V-shaped horizontal cross-sectional configuration. In the embodiment shown in FIG. 1, it is important that openings 18 and 20 be located entirely on one side of an imaginary vertical bisector of each of tubes 12 and 14, respectively. Preferably, the openings 18 and 20 will extend through an arc of no more than approximately 120 degrees.

Disposed in the aforementioned imaginary parallel horizontal planes between which openings 18 and 20 are located are first and second barrier bars 22 and 24, both of which extend back and forth in a plurality of interconnected short lengths between the first and second tubular sections 12 and 14. Barrier bars 22 and 24 serve to maintain tubular sections 12 and 14 in closely spaced relationship and also provide a barrier which will prevent a large piece of tissue or other material from covering openings 18 and 20.

Disposed inside of tubular section 14 is an irrigation tube designated generally by the numeral 26. Irrigation tube 26 comprises a fourth tubular section 28 which extends substantially the length of tubular section 14 and has an open end 30 to allow egress of fluid therefrom. Tubular section 28 merges into a Y 32 at the end opposite open end 30. A first arm 34 of Y 32 may be coupled with a tube 36 for continual introduction of antiseptic or antibiotic fluids. A second arm of 38 of Y 32 is provided with a fitting 40 of penetrable self-sealing material to permit injections to be made directly into tubular section 28.

When device 10 is placed in a cavity of the body to drain fluids therefrom, it will be appreciated that the construction substantially precludes the entry of loose material into openings 18 and 20 which would clog the openings and interfere with the drainage function. By utilizing two tubular sections in closely spaced parallel relationship, one section serves as a shield for the other section and the overall drainage capacity is increased. Drainage efficiency is also increased with device 10 by virtue of the fact that fluids may flow around and past one of the tubes and into the openings in the opposite tube in directions generally perpendicular to the direction of flow of fluid inside the tube. This phenomenon is illustrated by arrows A and B in FIG. 2. The ability of the fluid to flow directly into all of the openings 18 and 20 on an equal volume basis is to be contrasted with devices which may provide a shield over drain openings, but wherein the shield is closed except for being open on one end. A device of such a construction causes flow past the openings to be generally parallel to the flow of fluid in the tubes and the amount of fluid passing into the openings which are farthest removed from the shield openings is substantially less than the amount of fluid passing into openings near the shield opening. The overall effect is to substantially decrease the drainage efficiency when compared with the device of the present invention.

Figure 3:
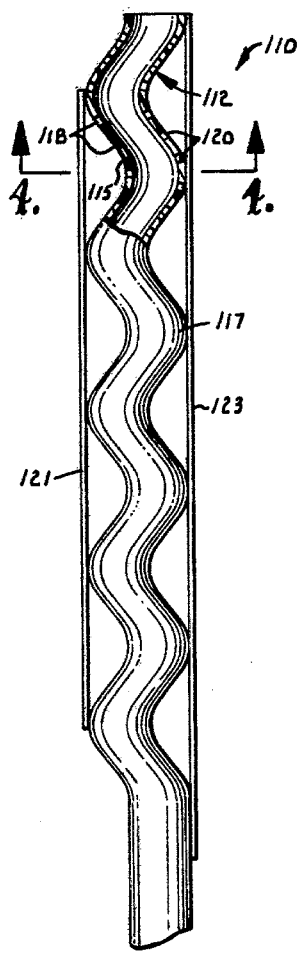
FIG. 3 is a side elevational view, with portions shown in cross-section, of an alternative embodiment of the improved drain construction.

An alternative embodiment of the invention is illustrated in FIG. 3 and designated generally by the numeral 110. Drainage device 110 comprises an elongated tubular section 112 which is disposed in a serpentine configuration with alternating concave and convex stretches 115 and 117 respectively. Tube 112 is open at one end and has a plurality of openings 118 and 120 disposed along the alternating concave stretches of opposite sides of the tube.

Extending longitudinally in parallel relationship on opposite sides of tube 112 and in contiguous relationship with opposed convex stretches 117 are first and second linear shields 121 and 123. It will be appreciated that shields 121 and 123 serve to maintain the serpentine configuration of tube 112 and also to partially protect openings 118 and 120 from the entry of loose material or impinging structures which would also clog the openings. As with the first embodiment described above, shields 121 and 123 permit fluids to pass by them and enter openings 118 and 120 at an angle relatively perpendicular to the direction of flow of fluid through the tube. Thus, fluid may flow equally into all of the openings throughout the length of tube 112 while the openings are protected, partially by the linear configuration of the tube and partially by shields 121 and 123 from the entry of material which would clog the openings.

Again, it is important that the openings lie on either side of an imaginary vertical bisector of tube 112, which bisector would extend perpendicularly relative to a supporting surface. The openings 118 and 120 are also located between imaginary parallel planes passing tangentially through points on opposite sides of the surface of tube 112. As with the embodiment described above, openings 118 and 120 may be of any desired configuration although the openings should not extend through an arc of greater than approximately 120 degrees.

It is also possible to insert an irrigation tube inside of tube 112 in the manner described above for irrigation tube 26. It will be appreciated that the irrigation tube could take many different forms and could extend past the drain tube if desired. The irrigation tube could also be operatively associated with the drain tube on the outside thereof.

Figure 5:
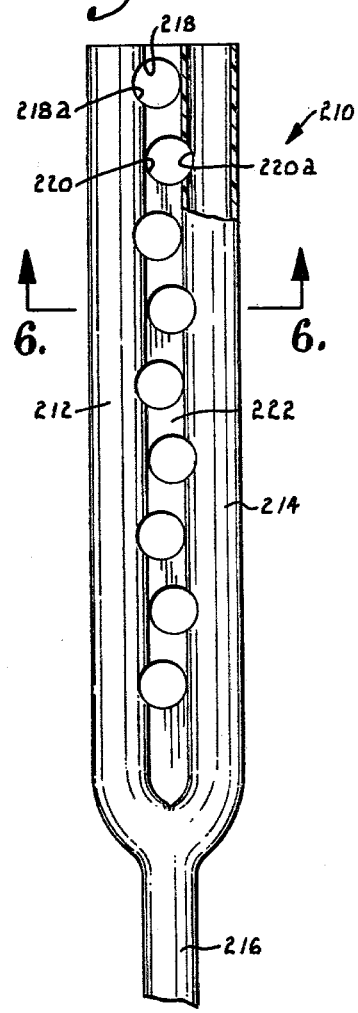
FIG. 5 is a side elevational view of another alternative embodiment of the improved drain construction.
Figure 6:
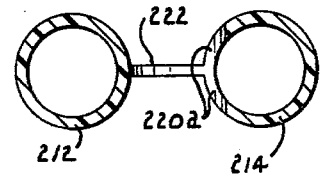
FIG. 6 is a horizontal cross-sectional view taken along line 6—6 of FIG. 5.

Another alternative embodiment of the invention is illustrated in FIGS. 5 and 6 and designated generally by the numeral 210. Device 210 comprises first and second elongated cylindrical tubular sections 212 and 214, respectively. The two sections are open at one end with the opposite end being coupled together in fluid relationship to form a common third tubular section 216. As with the tubular section 16 for the foregoing described embodiment, tubular section 216 may be of slightly larger diameter than each of the sections 212 and 214.

Referring additionally to FIG. 6, integral with and extending between tubular members 212 and 214 is a web portion 222, which holds the tubular sections in spaced apart relationship. Web portion 222 extends the length of the tubular members and is characterized by a plurality of openings 218 and 220. Web portion 222 extends in a generally horizontal plane at a point approximately bisecting the transverse dimensions of tubular members 212 and 214. It will thus be appreciated that web portion 222 is generally parallel to the aforementioned parallel imaginary planes, on either side of openings 218 and 220, which extend through opposed tangential points on the surfaces of the respective tubular members. Openings 218 extend through web portion 222 and also intersect the left hand tubular member 212. Thus an opening 218a into tubular member 212 is presented by each of the openings 218. Similarly, each of the openings 220 intersects with the right hand tubular member 214, and presents an opening 220a communicating with this tubular member. As best illustrated in FIG. 6, each of the openings 220a has upper and lower areas extending on either side of web portion 222 and both communicating with the area of tubular member 214. Similarly, the openings 218a each have upper and lower areas extending on either side of web portion 222 and communicating with the interior of tubular member 212. As with the aforedescribed embodiments, both sets of openings 218a and 220a are located entirely on one side of an imaginary vertical bisector of each respective tube. The openings also lie between parallel imaginary planes extending through opposed tangential points on the surfaces of the respective tubular members.

The device 210 is utilized in the same manner as the device 10 heretofore described. It will be appreciated that web portion 222 in addition to holding the two tubular members in spaced apart relationship along their longitudinal axes also presents a barrier means for at least partially blocking the openings 218a and 220a. Thus foreign material or body tissue which would tend to block the openings and close same to the flow of fluid is restrained by web portion 222. At most, a loose piece of foreign material or body tissue will only be able to block either the upper or lower area of each of the openings, while the other area will remain free to the flow of fluid into the tubular conduit.

As previously mentioned, the openings 218 and 220 including segments 218a and 220a may be of any desired configuration although with the embodiment 210 construction is facilitated by stamping the openings with the circular configuration illustrated. It is desirable that the openings 218a and 220a should not extend through an arc of the tubular member greater than approximately 120°.

It is also possible to insert an irrigation tube inside of one of the tubular members 212 or 214 in the manner described above for the device 10. Other modifications in the device 210 may be effected without departing from the scope of the invention.

While the invention has been described with particular reference to a surgical drain, it will be appreciated that the application of the principles involved in construction of the drain is not limited to surgical techniques and it is anticipated that the invention will be used in structural and geographical installations.

I claim:

1. A device for the passage of fluid between a congested area characterized by the presence of material capable of blocking the passage and an area removed from the congested area, said device comprising:

first and second tubular members each having a plurality of openings disposed along the length of the member; and means for holding said members in spaced apart lateral relationship along their longitudinal axes and for at least partially blocking said openings from the entry of material which would completely close said openings while accommodating free flow of fluid to said openings when no blocking material is present, each of said tubular members being characterized by a plurality of openings along its length for communication with one of said areas to receive a flow of fluid from said one area to the interior of said member, said openings being located on the side of said member which is facing the other member and between two parallel imaginary planes extending through opposed points on the surface of the member.

2. A device as set forth in claim 1, wherein said means for holding and blocking said members comprise a planar web portion extending transversely of said members and intersecting said openings whereby said openings extend on opposite sides of said web portion.

3. A device as set forth in claim 2, wherein said openings in one of said members are offset relative to the openings in the other of said members.

4. A device as set forth in claim 1, wherein said holding and blocking means comprises structure extending tangentially to said members across the space between said members, said structure having openings therein for communicating with the openings in said members.

5. A device as set forth in claim 4, wherein said holding and blocking means comprises a second structure extending tangentially to said members in parallel relationship to said first mentioned structure and spanning the space between said members, said second structure having openings therein for communicating with the openings in said members.

6. A device as set forth in claim 1, wherein said first and second tubular members are coupled with a third tubular member.

7. A device as set forth in claim 6, wherein is included a fourth tubular member extending inside of one of said first and second members, said fourth tubular member having a diameter smaller than the diameter of the one of said first and second members in which it is located and said fourth tubular member terminating at a point outside of the said member in which it is disposed.

* * * * *